United States Patent
Chang et al.

(10) Patent No.: US 10,117,595 B2
(45) Date of Patent: Nov. 6, 2018

(54) METHOD AND APPARATUS FOR DETECTING CARDIAC ARRHYTHMIA AND RECORDING MEDIUM USING THE METHOD

(71) Applicant: HTC Corporation, Taoyuan (TW)

(72) Inventors: Chih-Hung Chang, Taoyuan (TW); Emily Joanne Chang, San Jose, CA (US); Tung-Peng Wu, Taoyuan (TW)

(73) Assignee: HTC Corporation, Taoyuan (TW)

( * ) Notice: Subject to any disclaimer, the term of this patent is extended or adjusted under 35 U.S.C. 154(b) by 487 days.

(21) Appl. No.: 14/854,041

(22) Filed: Sep. 15, 2015

(65) Prior Publication Data

US 2017/0071482 A1    Mar. 16, 2017

(51) Int. Cl.
*A61B 5/046*        (2006.01)
*A61B 5/024*        (2006.01)
*A61B 5/0245*       (2006.01)

(52) U.S. Cl.
CPC .......... *A61B 5/046* (2013.01); *A61B 5/02416* (2013.01); *A61B 5/0245* (2013.01); *A61B 5/02405* (2013.01); *A61B 2560/0209* (2013.01)

(58) Field of Classification Search
CPC .... A61B 5/02405; A61B 5/046; A61B 5/0468
See application file for complete search history.

(56) References Cited

U.S. PATENT DOCUMENTS

| | | | | |
|---|---|---|---|---|
| 6,519,490 B1 * | 2/2003 | Wiesel | ............ | A61B 5/046 600/518 |
| 7,146,206 B2 * | 12/2006 | Glass | ............ | A61B 5/02405 600/521 |
| 7,706,868 B2 * | 4/2010 | Wiesel | ............ | A61B 5/046 600/518 |
| 7,751,876 B2 * | 7/2010 | Healey | ............ | A61B 5/0468 600/517 |
| 8,027,722 B1 * | 9/2011 | Nabutovsky | ......... | A61N 1/3622 607/14 |
| 9,408,576 B2 * | 8/2016 | Chon | ............ | A61B 5/7282 |
| 2005/0004486 A1 * | 1/2005 | Glass | ............ | A61B 5/02405 600/515 |
| 2007/0073176 A1 * | 3/2007 | Healey | ............ | A61B 5/0468 600/517 |
| 2009/0012412 A1 * | 1/2009 | Wiesel | ............ | A61B 5/024 600/508 |
| 2009/0275849 A1 * | 11/2009 | Stewart | ............ | A61B 5/02405 600/518 |

(Continued)

*Primary Examiner* — Meredith Weare
(74) *Attorney, Agent, or Firm* — JCIPRNET (57) ABSTRACT

A method and an apparatus for detecting cardiac arrhythmia and a recording medium using the method are provided. In the method, physiological signals of a human comprising a sequence of heart pulses are acquired, and an average of heartbeat intervals between pairs of consecutive heart pulses in the sequence of heart pulses is calculated. Each pair of consecutive heartbeat intervals is examined to identify premature ventricular contraction (PVC) candidates or atrial premature contraction (APC) candidates based on whether a difference between the pair of consecutive heartbeat intervals is larger than a product of a factor and the average of heartbeat intervals and whether an average of the pair of consecutive heartbeat intervals is within a predetermined range.

15 Claims, 5 Drawing Sheets

(56) References Cited

U.S. PATENT DOCUMENTS

2013/0172765 A1* 7/2013 Stewart .............. A61B 5/02405
600/513
2014/0330134 A1* 11/2014 Chon ................... A61B 5/7282
600/479

* cited by examiner

METHOD AND APPARATUS FOR DETECTING CARDIAC ARRHYTHMIA AND RECORDING MEDIUM USING THE METHOD

BACKGROUND

Atrial fibrillation (AF) is known as the most common arrhythmia in adults, and it is estimated that millions of people suffer from AF. Previous studies reported that AF may increase risk for other diseases such as stroke, cardiovascular mortality, and obstructive sleep apnea.

Cardiac rhythms of patients with AF possess two particular characteristics: (i) R-R interval irregularity; and (ii) absence of P waves. Although the absence of P waves is a primary indicator of AF, P waves are low amplitude which makes them difficult to analyze due to high intensity noise in electrocardiograms (ECGs) derived from ambulatory electrocardiography. Compared to P waves, R waves have much higher amplitudes and therefore higher tolerance to ECG noise, making detection mush easier. Consequently, using R-R intervals to detect AF is considered to be the most robust approach.

Accordingly, several AF detection methods based on R-R interval irregularity have been proposed. However, the R-R interval window length required for those methods varies from 32 beats to 128 beats. To exhibit high accuracy and finer temporal resolution for real-time monitoring and shorter AF episodes detection, computational complexity together with the power consumption is dramatically increased.

SUMMARY

To sustain long operational time, the disease diagnosis devices must consume low power, reduce memory use, and minimize data transmission. Accordingly, the disclosure provides a method and an apparatus for detecting cardiac arrhythmia and a recording medium using the method, through which computational complexity can be reduced and accuracy of short AF episodes detection can be enhanced.

The disclosure provides a method for detecting cardiac arrhythmia, adapted for an electronic apparatus. In the method, physiological signals of a human comprising a sequence of heart pulses are acquired, and an average of heartbeat intervals between pairs of consecutive heart pulses in the sequence of heart pulses is calculated. Each pair of consecutive heartbeat intervals is examined to determine whether a difference between the pair of consecutive heartbeat intervals is larger than a product of a first factor and the average of heartbeat intervals and determine whether an average of the pair of consecutive heartbeat intervals is within a predetermined range, wherein an upper limit of the predetermined range is a product of a second factor and the average of heartbeat intervals and a lower limit of the predetermined range is a product of a third factor and the average of heartbeat intervals. A heartbeat between the pair of consecutive heartbeat intervals is identified as a premature ventricular contraction (PVC) candidate or a atrial premature contraction (APC) if the difference between the pair of consecutive heartbeat intervals is larger than the product of the first factor and the average of heartbeat intervals and the average of the pair of consecutive heartbeat intervals is within the predetermined range.

In an example of the present disclosure, after the step of identifying the heartbeat between the pair of consecutive heartbeat intervals as the PVC candidate or the APC candidate, a pulse interval irregularity among the heartbeat intervals excluding the pairs of consecutive heartbeat intervals associated with the PVC candidate or the APC candidate is calculated and it is determined that there is an atrial fibrillation (AF) detected from the physiological signals in response to a determination that the pulse interval irregularity is larger than a threshold.

In an example of the present disclosure, before the step of calculating the average of heartbeat intervals between pairs of consecutive heart pulses in the sequence of heart pulses, a pulse interval irregularity among the heartbeat intervals between the pairs of consecutive heart pulses in the sequence of heart pulses is calculated and it is determined that there is no AF detected from the physiological signals in response to a determination that the pulse interval irregularity is not larger than the threshold.

In an example of the present disclosure, after the step of identifying the beat between the pair of consecutive heartbeat intervals as the PVC candidate or the APC candidate, a previous heartbeat interval consecutive to a former heartbeat interval of the pair of consecutive heartbeat intervals is searched and the previous heartbeat interval and a later heartbeat interval of the pair of consecutive heartbeat intervals are examined to identify whether the beat between the previous heartbeat interval and the later heartbeat interval is the PVC candidate or the APC candidate.

The disclosure provides an apparatus for detecting cardiac arrhythmia, which comprises a calculation module, an identifying module, and a detection module. The calculation module is configured to acquire physiological signals of a human comprising a sequence of heart pulses, and calculate an average of heartbeat intervals between pairs of consecutive heart pulses in the sequence of heart pulses, a difference between each pair of consecutive heartbeat intervals and an average of each pair of consecutive heartbeat intervals. The identifying module is configured to examine each pair of consecutive heartbeat intervals and identify a heartbeat between the pair of consecutive heartbeat intervals as a PVC candidate or an APC candidate if the difference between the pair of consecutive heartbeat intervals is larger than a product of a first factor and the average of heartbeat intervals and the average of the pair of consecutive heartbeat intervals is within a predetermined range, wherein an upper limit of the predetermined range is a product of a second factor and the average of heartbeat intervals and a lower limit of the predetermined range is a product of a third factor and the average of heartbeat intervals.

In an example of the present disclosure, the apparatus further comprises a detection module which is configured to calculate a pulse interval irregularity among the heartbeat intervals excluding the pairs of consecutive heartbeat intervals associated with the PVC candidate or the APC candidate, and determine there is an AF detected from the physiological signals in response to a determination that the pulse interval irregularity is larger than a threshold.

In an example of the present disclosure, the detection module further calculates a pulse interval irregularity among the heartbeat intervals between the pairs of consecutive heart pulses in the sequence of heart pulses after the calculation module acquires physiological signals, and determines there is no AF detected from the physiological signals in response to a determination that the pulse interval irregularity is not larger than the threshold.

In an example of the present disclosure, the identifying module further searches a previous heartbeat interval consecutive to a former heartbeat interval of the pair of consecutive heartbeat intervals, and examines the previous heartbeat interval and a later heartbeat interval of the pair of consecutive heartbeat intervals to identify whether the beat between the previous heartbeat interval and the later heartbeat interval is the PVC candidate or the APC candidate.

In an example of the present disclosure, the pulse interval irregularity comprises a normalized absolute difference (NADiff) or a root mean square of the successive differences (RMSSD) of heartbeat intervals.

In an example of the present disclosure, a value of the first factor is ranging from 0.3 to 0.4, a value of the second factor is ranging from 0.8 to 0.95, and a value of the third factor is ranging from 1.1 to 1.2.

The disclosure provides a non-transitory computer readable medium in which a computer program is recorded. The computer program is loaded by an electronic apparatus to execute the following steps. First, physiological signals of a human comprising a sequence of heart pulses are acquired, and an average of heartbeat intervals between pairs of consecutive heart pulses in the sequence of heart pulses is calculated. Then, each pair of consecutive heartbeat intervals is examined to determine whether a difference between the pair of consecutive heartbeat intervals is larger than a product of a first factor and the average of heartbeat intervals and determine whether an average of the pair of consecutive heartbeat intervals is within a predetermined range, wherein an upper limit of the predetermined range is a product of a second factor and the average of heartbeat intervals and a lower limit of the predetermined range is a product of a third factor and the average of heartbeat intervals. A heartbeat between the pair of consecutive heartbeat intervals is identified as a PVC candidate or an APC candidate if the difference between the pair of consecutive heartbeat intervals is larger than the product of the first factor and the average of heartbeat intervals and the average of the pair of consecutive heartbeat intervals is within the predetermined range.

Based on the above, in the method and an apparatus for detecting cardiac arrhythmia and a recording medium using the method provided by the present disclosure, a low-power scheme is proposed to quickly screen cardiac arrhythmia on the devices. Only when a signal segment is identified as a cardiac arrhythmia suspect will the device record and transmit the signal. Accordingly, the resource requirement on the device is reduced and the operation time of the device is prolonged.

In order to make the aforementioned and other features and advantages of the invention more comprehensible, several examples accompanied with figures are described in detail below.

BRIEF DESCRIPTION OF THE DRAWINGS

The accompanying drawings are included to provide a further understanding of the invention, and are incorporated in and constitute a part of this specification. The drawings illustrate examples of the invention and, together with the description, serve to explain the principles of the invention.

DESCRIPTION OF EXAMPLES

A typical premature ventricular contraction (PVC) heartbeat may exhibit several features such as (i) a broad QRS complex (i.e. larger than 120 ms); (ii) an abnormal ST segment and various T waves; (iii) early R wave occurrence (i.e. earlier than the next expected sinus impulse); and (iv) following a full compensatory pause. Besides, a typical atrial premature contraction (APC) may also exhibit aforesaid features (iii) and (iv). Based on these features, typical PVCs and APCs may be characterized by a shorter heartbeat interval (e.g. R-R interval in ECG signals) followed by a longer heartbeat interval. The PVCs and APCs may increase the numbers of short and long heartbeat intervals in an ECG signal, potentially leading to high pulse interval irregularity. Accordingly, the present disclosure screens the PVCs and APCs to prevent false detection of atrial fibrillation (AF). Since a PVC or APC heartbeat usually follows a full compensatory pause, the sum of the heartbeat intervals around the PVC or APC is almost double the preceding heartbeat interval. This difference occurs because the sinus node is not affected by a premature contraction and continues to produce an impulse at the expected time. Therefore, a PVC or APC would shorten the preceding heartbeat interval while simultaneously lengthening the following heartbeat interval, and the sum of these two heartbeat intervals would be approximately double the preceding heartbeat interval.

Based on the above observation, the present disclosure provides a novel cardiac arrhythmia detection method, in which characteristics of heartbeat intervals in the physiological signals of a human are used to examine PVCs and APCs. The examination result is further combined with the detection on the irregularity of heartbeat intervals to detect the AF. As a result, the beats associated with the PVC or the APC that severely affect the detection of AF are removed and therefore an accuracy of AF detection can be increased.

Figure 1:
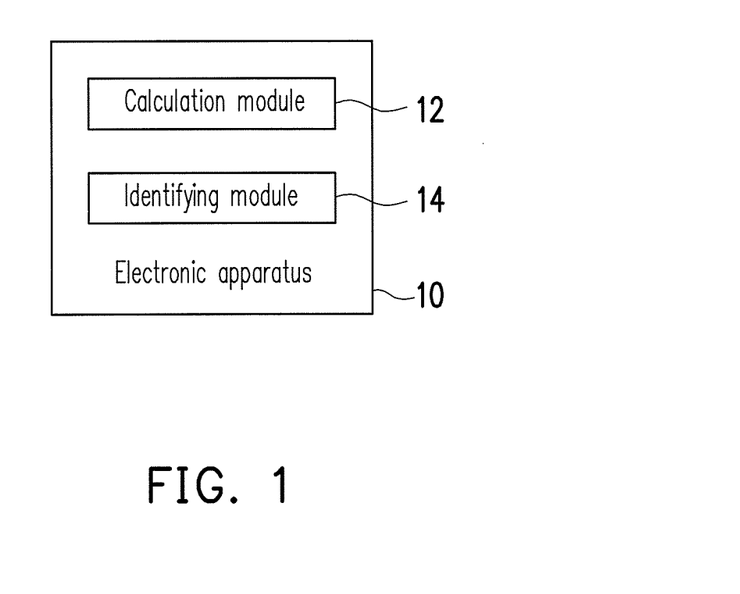
FIG. 1 is a block diagram of an electronic apparatus according to an example of the disclosure.

FIG. 1 is a block diagram of an electronic apparatus according to an example of the disclosure. With reference to FIG. 1, in the present example, the electronic apparatus 10 is, for example, a smartphone, a PDA, a tablet PC, a computer, a smart watch or any other disease diagnosis apparatus, and includes a calculation module 12 and an identifying module 14. Those modules are, for example, hardware components such as circuits or software programs stored in the electronic apparatus 10 that can be loaded by the processor (not shown) of the electronic apparatus 10 such as a central processing unit (CPU), so as to execute functions of the method for detecting AF. Examples are provided hereinafter to describe the detailed steps of the method.

Figure 2:
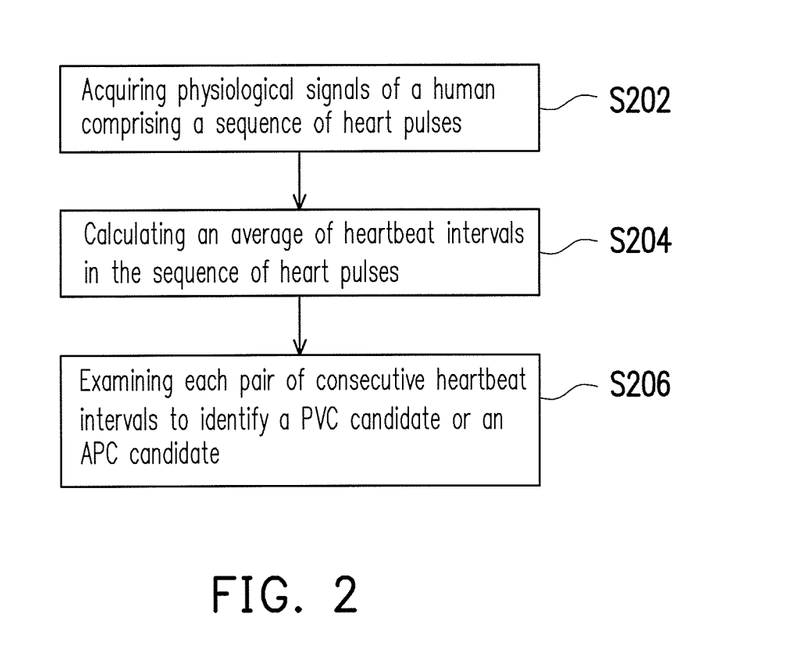
FIG. 2 is a flowchart illustrating a method for detecting cardiac arrhythmia according to an example of the disclosure.

FIG. 2 is a flowchart illustrating a method for detecting cardiac arrhythmia according to an example of the disclosure. Referring to FIG. 1 and FIG. 2 together, the method of the present example is adapted for the electronic apparatus 10 of FIG. 1. Detailed steps in the method of the present embodiment are described below with reference to each component of the electronic apparatus 10 depicted in FIG. 1.

First, the calculation module 12 acquires physiological signals of a human comprising a sequence of heart pulses (step S202). The physiological signals may be electrocardiograms (ECG) signals, Photoplethysmography (PPG) signals, or other electrical signals of cardiac activity, which are obtained though measuring the electrical potential difference across the heart by two or more electrodes or other sensing devices. The physiological signals may be acquired from measurements of the electronic apparatus 10 itself or acquired from measurements uploaded by a remote device through a network, which is not limited herein.

Figure 3:
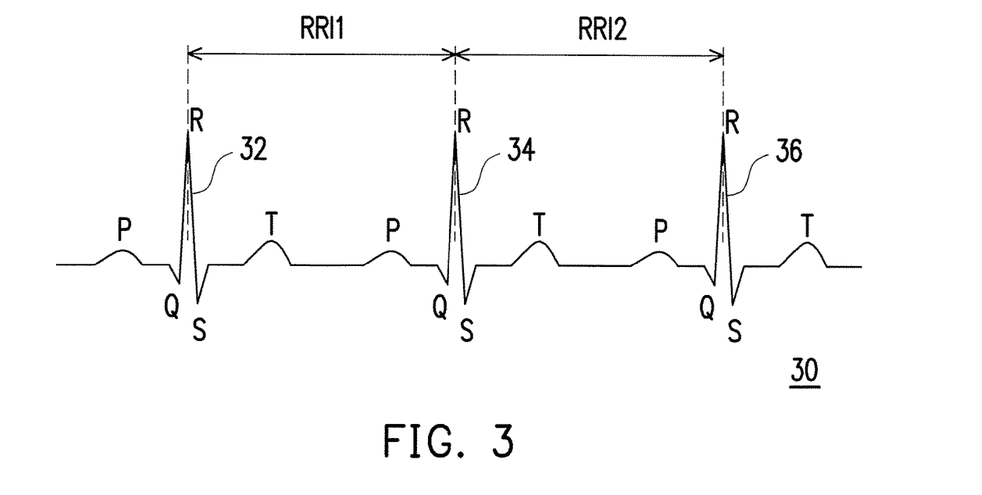
FIG. 3 is an example of ECG signals according to an example of the disclosure.
Figure 4:
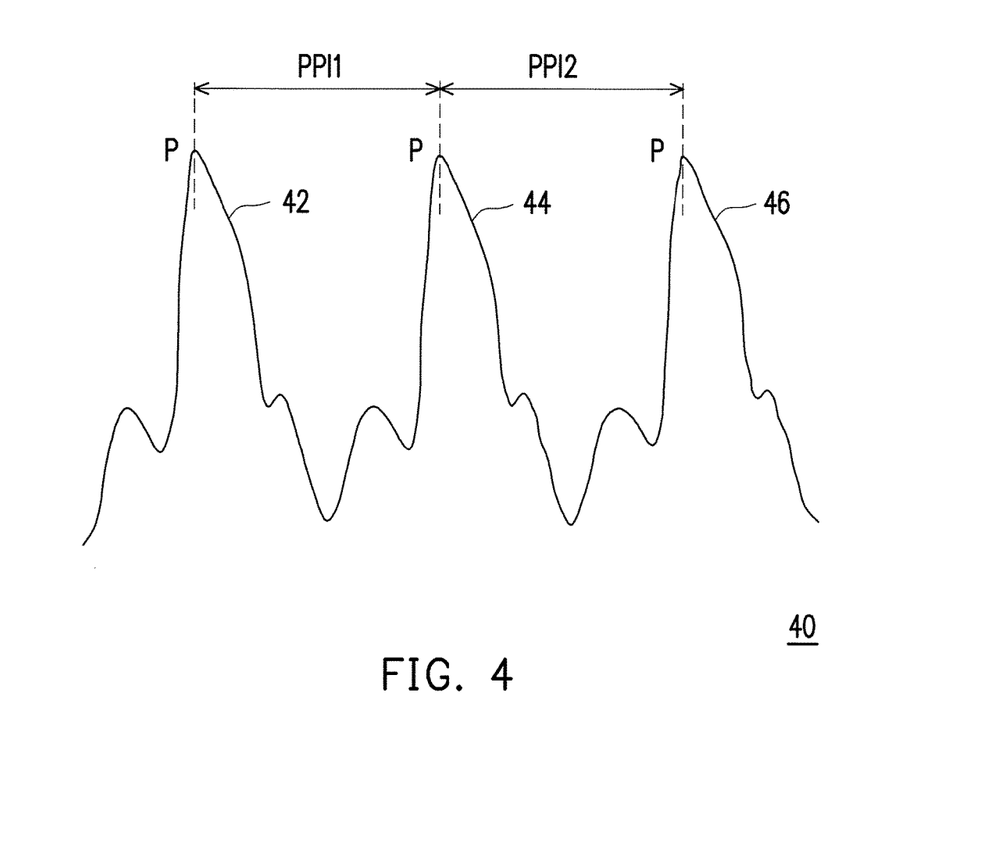
FIG. 4 is an example of PPG signals according to an example of the disclosure.

For example, FIG. 3 is an example of ECG signals according to an example of the disclosure, and FIG. 4 is an example of PPG signals according to an example of the disclosure. Referring to FIG. 3, the ECG signals 30 comprises a sequence of heart pulses 32, 34 and 36, and each heart pulse comprises a P wave, a Q wave, an R wave, a S wave and a T wave. An interval between each pair of consecutive R waves is defined as an R-R interval (RRI), such as an R-R interval RRI 1 between R wave of heart pulse 32 and R wave of heart pulse 34, or an R-R interval RRI 2 between R wave of heart pulse 34 and R wave of heart pulse 36. Referring to FIG. 4, the PPG signals 40 comprises a sequence of heart pulses 42, 44 and 46, and each heart pulse comprises a peak P. An interval between each pair of consecutive peaks is defined as a heartbeat interval, such as a peak-to-peak interval PPI 1 between peaks of heart pulse 42 and heart pulse 44, or a peak-to-peak interval PPI 2 between peaks of heart pulse 44 and heart pulse 46.

Next, the calculation module 12 calculates an average of heartbeat intervals in the sequence of heart pulses (step S204) as a reference. The calculation module 12 may further calculate a difference between each pair of consecutive heartbeat intervals and an average of each pair of consecutive heartbeat intervals for the use of later comparison.

It is noted that, in one embodiment, the calculation module 12 may calculate an average of the heartbeat intervals in the sequence of heart pulses of the whole acquired physiological signals and provide the calculated average for the identifying module 104 to identify cardiac arrhythmia in the physiological signals. However, in another embodiment, the calculation module 12 may calculate an average of heartbeat intervals by segments of the acquired physiological signals. That is to say, the calculation module 12 may calculate an average of heartbeat intervals in the sequence of heart pulses in each segment of the acquired physiological signals and provide the calculated averages for the identifying module 104 to identify the cardiac arrhythmia in each segment of the acquired physiological signals. Each segment may contain a specific number of heart pulses such as 10 or 20 heart pulses, but the application is not limited thereto.

Finally, the identifying module 104 examines each pair of consecutive heartbeat intervals in the sequence of heart pulses to identify a PVC candidate or an APC candidate (step S206). To be specific, the identifying module 104 may retrieve the calculation results outputted by the calculation module 12 and execute a PVC or APC candidate identifying procedure in a manner of pair by pair of consecutive heartbeat intervals.

For each pair of consecutive heartbeat intervals, the identifying module 104 determines whether a difference between the pair of consecutive heartbeat intervals is larger than a product of a first factor and the average of heartbeat intervals, in which the value of the first factor is ranging from 0.3 to 0.4, but is not limited thereto. The identifying module 104 further determines whether an average of the pair of consecutive heartbeat intervals is within a predetermined range, in which an upper limit of the predetermined range is a product of a second factor and the average of heartbeat intervals and a lower limit of the predetermined range is a product of a third factor and the average of heartbeat intervals. The value of the second factor is ranging from 0.8 to 0.95, especially 0.9, while the value of the third factor is ranging from 1.1 to 1.2, especially 1.15, but is not limited thereto.

For example, given a sequence of N R-R intervals (RRIs) in ECG signals, an average of these N RRIs is first calculated, denoted as $RRI_{avg}$, and then every pair of consecutive RRIs is examined, in which if two consecutive RRIs, denoted as $RRI_a$ and $RRI_b$, meet the following conditions (1) and (2), the heartbeat between the RRIs is identified as a PVC candidate or a APC candidate.

$$(RRI_b - RRI_a) > 0.4 \times RRI_{avg} \tag{1}$$

$$0.9 \times RRI_{avg} < (RRI_a + RRI_b)/2 < 1.15 \times RRI_{avg} \tag{2}$$

It is noted that the PVCs or APCs may occur once or consecutively (i.e. generally referred to as couplet or triplet PVCs), and therefore when a PVC candidate or an APC candidate is identified, the identifying module 104 may further search a previous heartbeat interval consecutive to a former heartbeat interval of the pair of consecutive heartbeat intervals associated with the PVC candidate or the APC candidate, and examine the previous heartbeat interval and a later heartbeat interval of the pair of consecutive heartbeat intervals to identify whether the beat between the previous heartbeat interval and the later heartbeat interval is the PVC candidate or the APC candidate. The further searching and examination may be executed once or twice so as to find the existence of couplet or triplet PVCs or APCs.

Referring back to the previous example, for two consecutive RRIs, denoted as $RRI_a$ and $RRI_b$, once the PVC candidate or the APC candidate is identified, a compensatory pause (i.e. the $RRI_b$) is also found, the $RRI_b$ is temporarily stored while the $RRI_a$ is removed. A backward search is executed to search any possible PVC or APC heartbeats until no PVC is found. When no PVC or APC is found, the temporarily stored $RRI_b$ is removed to prevent a subsequently calculated pulse interval irregularity from being affected by the PVCs or APCs.

Figure 5:
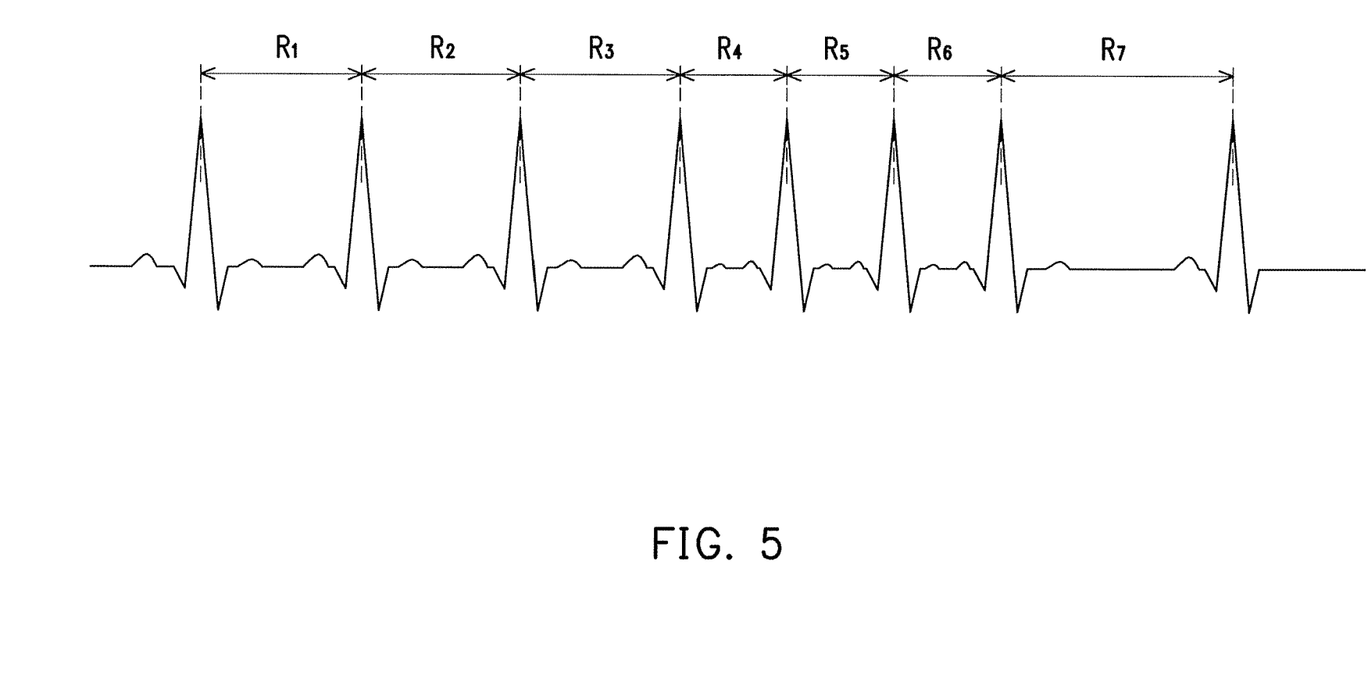
FIG. 5 is an example illustrating a method for identifying PVCs on consecutive heartbeat intervals according to an example of the disclosure.

FIG. 5 is an example illustrating a method for identifying PVCs on consecutive R-R intervals in ECG signals according to an example of the disclosure. Referring to FIG. 5, a sequence of heart pulses of ECG signals is shown, in which the heart pulses form RRIs R1 to R7. When executing the PVC identification, a first pair of consecutive RRIs R1 and R2 is examined by using aforesaid conditions (1) and (2). Since the lengths of RRIs R1 and R2 are close to each other, it is determined that no PVC is identified between RRIs R1 and R2. Similarly, the second pair of consecutive RRIs R2 and R3 is also examined to have no PVC. As for the pair of consecutive RRIs R3 and R4, since the RRI R3 is larger than the RRI R4, the difference of RRI R3 subtracted from RRI R4 is a negative value, which does not meet the condition (1) and therefore it is determined that no PVC is identified between the RRIs R3 and R4. As for the pair of consecutive RRIs R4 and R5 and the pair of consecutive RRIs R5 and R6, since the lengths of the RRIs R4, R5 and R6 are close to each other, it is determined that no PVC is identified between the RRIs R4 to R6. However, as for the pair of consecutive RRIs R6 and R7, the difference of RRI R7 subtracted from RRI R6 is a positive value meets the condition (1) and the average of RRIs R6 and R7 meets the condition (2), and therefore it is determined there is a PVC between the pair of RRIs R6 and R7.

It is noted, after identifying the PVC between the pair of RRIs R6 and R7, the later RRI R7 is determined as a compensatory pause and temporarily stored, and the former RRI R6 is removed. A previous RRI R5 consecutive to RRI R6 of the pair of RRIs R6 and R7 is searched and examined with RRI R7 to identify whether there are PVCs between RRIs R5 and R7. Since the difference and the average of RRIs R5 and R7 meet the conditions (1) and (2), it is determined that there are PVCs between RRIs R5 and R7, and accordingly the RRI R5 is removed. Then, a further previous RRI R4 consecutive to RRI R5 is searched and examined with RRI R7 to identify whether there are PVCs between RRIs R4 and R7, and accordingly the RRI R4 is removed. Since the difference and the average of RRIs R4 and R7 meet the conditions (1) and (2), it is determined that there are PVCs between RRIs R4 and R7. In the present example, the previous RRI searching is executed twice so as to find the existence of triplet PVCs. It is noted that when no PVC is found when executing the previous RRI searching, the PVC identification with respect to the later RRI R7 is ended and the later RRI R7 is removed.

In aforesaid embodiment, when a PVC is determined between RRIs, the former RRI (e.g. RRI R5 or RRI R4) is removed to avoid misjudgments in the subsequent examination. However, in another embodiment, the RRIs may be kept (i.e. not removed) in the sequence of heart pulses, but will be labeled so as to be excluded from the subsequent examination to prevent a subsequently calculated pulse interval irregularity from being affected by the PVCs or APCs.

After the PVC candidates and APC candidates are identified, a pulse interval irregularity used for identifying an atrial fibrillation (AF) is further calculated based on the heartbeat intervals excluding the pairs of consecutive heartbeat intervals associated with the PVC candidate and the APC candidate. An example is given below for further illustration.

Figure 6:
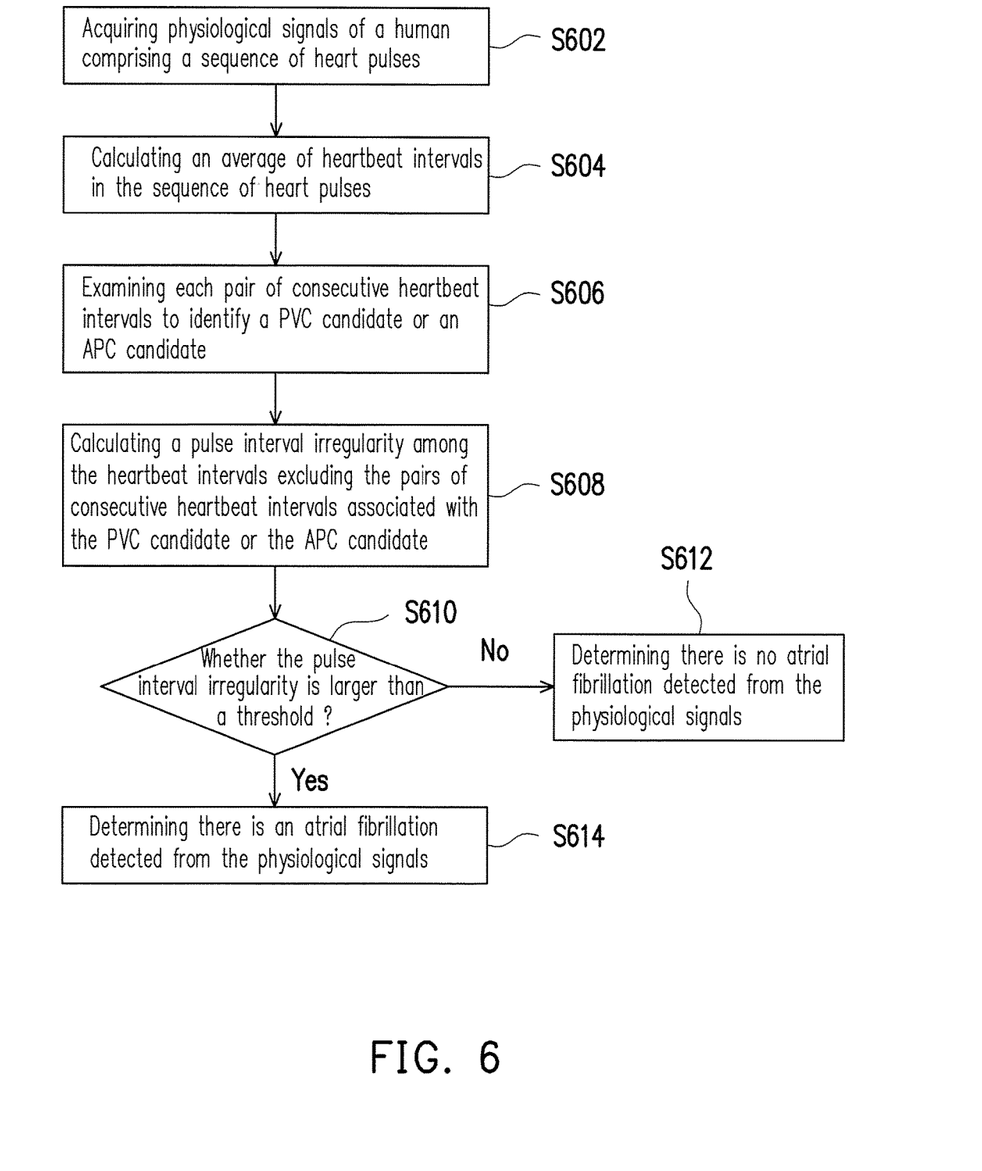
FIG. 6 is a flowchart illustrating a method for detecting AF according to an example of the disclosure.

FIG. 6 is a flowchart illustrating a method for detecting AF according to an example of the disclosure. Referring to FIG. 1 and FIG. 6 together, the method of the present example is adapted for the electronic apparatus 10 of FIG. 1. Detailed steps in the method of the present embodiment are described below with reference to each component of the electronic apparatus 10 depicted in FIG. 1.

First, the calculation module 12 acquires physiological signals of a human comprising a sequence of heart pulses (step S602). Next, the calculation module 12 calculates an average of heartbeat intervals in the sequence of heart pulses (step S604). Then, the identifying module 104 examines each pair of consecutive heartbeat intervals in the sequence of heart pulses to identify a PVC candidate or an APC candidate (step S606). The steps S602 to S606 are the same as or similar to the steps S202 to S206 in the previous example, thus the details are not repeated herein.

After every pair of consecutive heartbeat intervals are examined, a detection module (not shown) of the electronic apparatus 10 calculates a pulse interval irregularity among the heartbeat intervals excluding the pairs of consecutive heartbeat intervals associated with the PVC candidate or the APC candidate (step S608), and determines whether the pulse interval irregularity is larger than a threshold (step S610). If the pulse interval irregularity is determined as larger than the threshold, the detection module 16 determines there is an AF detected from the physiological signals (step S612). Otherwise, if the pulse interval irregularity is determined as not larger than the threshold, the detection module 16 determines there is no AF detected from the physiological signals (step S614). The pulse interval irregularity is, for example, a normalized absolute difference (NADiff) or a root mean square of the successive differences (RMSSD) of heartbeat intervals, which is no limited thereto.

In detail, in the present example, the pulse interval irregularity is used to detect AF. While calculating the pulse interval irregularity, the pulse intervals (i.e. heartbeat intervals) associated with the PVC or APC are excluded to increase the false detection rate.

Taking the NADiff for example, given a sequence of N heartbeat intervals (RRIs), the NADiff of consecutive heartbeat intervals is defined as:

$$NADiff = \frac{\sum_{i=1}^{i=N-1} |RRI_{i+1} - RRI_i|}{\sum_{i=1}^{i=N} RRI_i} \qquad (3)$$

Normal sinus rhythms exhibit more regular heartbeat intervals and hence smaller NADiff, whereas AF rhythms exhibit larger NADiff due to heartbeat interval irregularity. Instead of constraining the heartbeat intervals to avoid non-AF rhythms and noise that comes with ECG measurements, the typical PVCs and APCs that severely affect the value of NADiff are removed in NADiff calculation. As a result, the false detection resulting from the PVC and APC heartbeats can be avoided and the false detection rate can be increased.

In aforesaid example, the calculation of pulse interval irregularity is executed after the PVC and APC examination so as to avoid false detection due to PVC and APC heartbeats. However, in another example, the calculation of pulse interval irregularity may be additionally executed before the PVC and APC examination so as to exclude non-AF segments.

Figure 7:
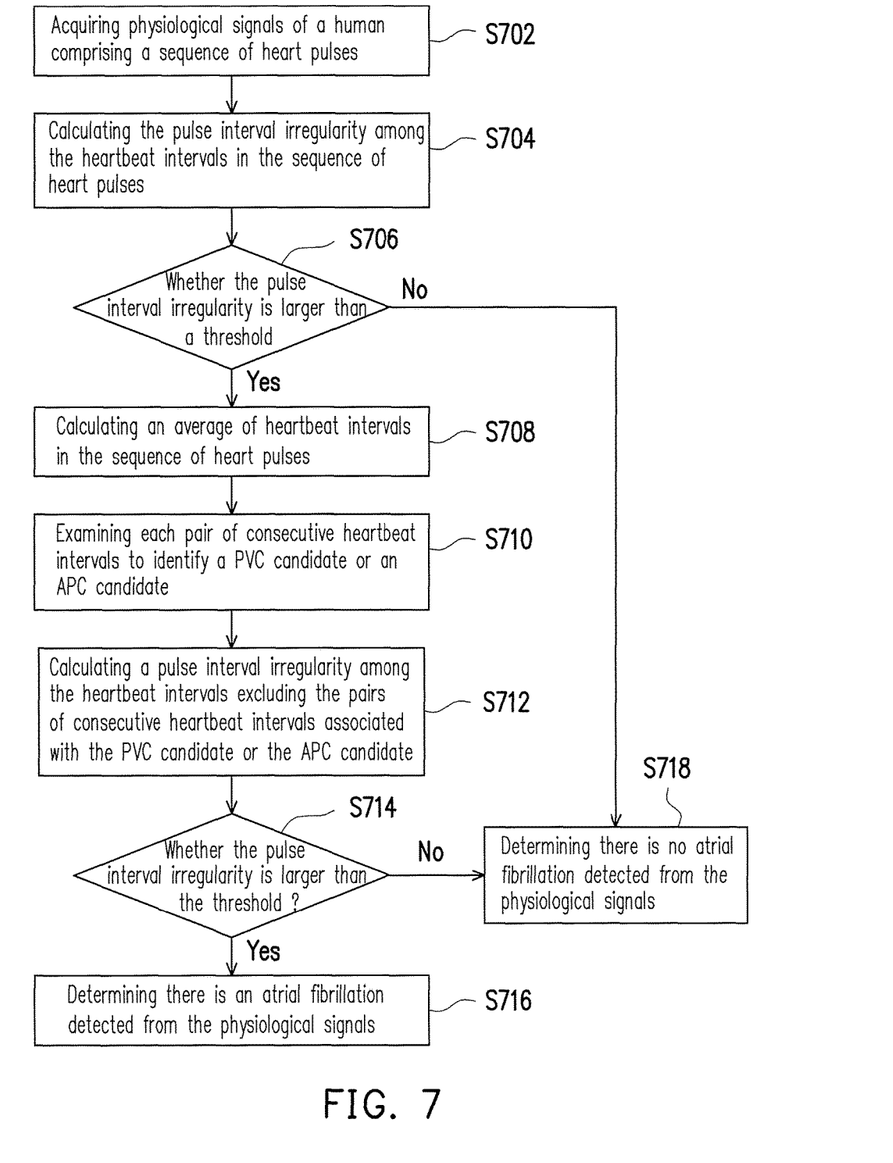
FIG. 7 is a flowchart illustrating a method for detecting AF according to an example of the disclosure.

In detail, FIG. 7 is a flowchart illustrating a method for detecting AF according to an example of the disclosure. Referring to FIG. 1 and FIG. 4 together, the method of the present example is adapted for the electronic apparatus 10 of FIG. 1. Detailed steps in the method of the present embodiment are described below with reference to each component of the electronic apparatus 10 depicted in FIG. 1.

First, the calculation module 12 acquires physiological signals of a human comprising a sequence of heart pulses (step S702). Then, the detection module 16 calculates a pulse interval irregularity among the heartbeat intervals in the sequence of heart pulses (step S704), and determines whether the pulse interval irregularity is larger than a threshold (step S706). If the pulse interval irregularity is determined as not larger than the threshold, the detection module 16 determines there is no AF detected from the physiological signals (step S718). The pulse interval irregularity is, for example, a normalized absolute difference (NADiff) or a root mean square of the successive differences (RMSSD) of heartbeat intervals, which is no limited thereto.

On the other hand, if the pulse interval irregularity is determined as larger than the threshold, the calculation module 12 calculates an average of heartbeat intervals in the sequence of heart pulses (step S708) as a reference. The calculation module 12 may further calculate a difference between each pair of consecutive heartbeat intervals and an average of each pair of consecutive heartbeat intervals for the use of later comparison. Then, the identifying module 104 examines each pair of consecutive heartbeat intervals in the sequence of heart pulses to identify a PVC candidate or an APC candidate (step S710).

The detection module 16 calculates a pulse interval irregularity among the heartbeat intervals excluding the pairs of consecutive heartbeat intervals associated with the PVC candidate or the APC candidate (step S712), and determines whether the pulse interval irregularity is larger than a threshold (step S714). If the pulse interval irregularity is determined as larger than the threshold, the detection module 16 determines there is an AF detected from the physiological signals (step S716). Otherwise, if the pulse interval irregularity is determined as not larger than the threshold, the detection module 16 determines there is no AF detected from the physiological signals (step S718). Steps S708 to S718 are the same as or similar to steps S604 to S612 in the embodiment described above and therefore will not be described herein.

Through aforesaid method, signal segments that are AF negative are pruned to skip the calculation on non-AF segments. The further PVC and APC examination is only executed on the rest signal segments, thus achieving low computational complexity.

The present disclosure further provides a non-transitory computer readable medium in which a computer program is record. The computer program is used to execute each step in the cardiac arrhythmia detection method as described above. The computer program is composed of a plurality of program code sections (i.e., building an organization diagram program code section, approving a list program code section, setting a program code section, and deploying a program code section). Moreover, after the program code sections are loaded into the electronic apparatus and executed, the steps in the cardiac arrhythmia detection method may be implemented.

To sum up, in the method and the apparatus for detecting cardiac arrhythmia and a recording medium using the method provided by the disclosure, the pulse interval irregularity detection is combined with the PVC and APC examination to ease the interference of PVCs and APCs. A robust algorithm is employed to examine the PVC and APC, such that no PVCs, APCs, or any other heartbeats are excluded due to constraint on the heartbeat intervals in conventional method. As such, both low computational complexity and short AF episode detection accuracy can be achieved.

Although the invention has been described with reference to the above examples, it will be apparent to one of the ordinary skill in the art that modifications to the described example may be made without departing from the spirit of the invention. Accordingly, the scope of the invention will be defined by the attached claims not by the above detailed descriptions.

What is claimed is:

1. A method for detecting cardiac arrhythmia, adapted for an electronic apparatus, comprising:
   acquiring physiological signals of a human comprising a sequence of heart pulses;
   calculating an average of heartbeat intervals in the sequence of heart pulses;
   examining each pair of consecutive heartbeat intervals to determine whether a difference between the pair of consecutive heartbeat intervals is larger than a product of a first factor and the average of heartbeat intervals and determine whether an average of the pair of consecutive heartbeat intervals is within a predetermined range, wherein an upper limit of the predetermined range is a product of a second factor and the average of heartbeat intervals and a lower limit of the predetermined range is a product of a third factor and the average of heartbeat intervals; and
   identifying a heartbeat between the pair of consecutive heartbeat intervals as a premature ventricular contraction (PVC) candidate or an atrial premature contraction (APC) candidate in response to a determination that the difference between the pair of consecutive heartbeat intervals is larger than the product of the first factor and the average of heartbeat intervals and the average of the pair of consecutive heartbeat intervals is within the predetermined range,
   wherein after the step of identifying the heartbeat between the pair of consecutive heartbeat intervals as the PVC candidate or the APC candidate, the method further comprises:
   calculating a first pulse interval irregularity among the heartbeat intervals excluding the pair of consecutive heartbeat intervals associated with the PVC candidate or the APC candidate; and
   determining there is an atrial fibrillation (AF) detected from the physiological signals in response to a determination that the first pulse interval irregularity is larger than a threshold.

2. The method according to claim 1, wherein the method further comprises:
   calculating a second pulse interval irregularity among the heartbeat intervals in the sequence of heart pulses; and
   determining there is no AF detected from the physiological signals in response to a determination that the second pulse interval irregularity is not larger than the threshold.

3. The method according to claim 1, wherein after the step of identifying the heartbeat between the pair of consecutive heartbeat intervals as the PVC candidate or the APC candidate, the method further comprises:
   searching a previous heartbeat interval consecutive to a former heartbeat interval of the pair of consecutive heartbeat intervals; and
   examining the previous heartbeat interval and a later heartbeat interval of the pair of consecutive heartbeat intervals to identify whether the heartbeat between the previous heartbeat interval and the later heartbeat interval is the PVC candidate or the APC candidate.

4. The method according to claim 1, wherein the first pulse interval irregularity comprises a normalized absolute difference (NADiff) or a root mean square of the successive differences (RMSSD) of heartbeat intervals.

5. The method according to claim 1, wherein a value of the first factor is ranging from 0.3 to 0.4.

6. The method according to claim 1, wherein a value of the second factor is ranging from 0.8 to 0.95.

7. The method according to claim 1, wherein a value of the third factor is ranging from 1.1 to 1.2.

8. An apparatus for detecting cardiac arrhythmia, comprising:
   a processor, configured to acquire physiological signals of a human comprising a sequence of heart pulses, and calculate an average of heartbeat intervals between pairs of consecutive heart pulses in the sequence of heart pulses, a difference between each pair of consecutive heartbeat intervals and an average of each pair of consecutive heartbeat intervals,
   wherein the processor is further configured to examine each pair of consecutive heartbeat intervals and identify a heartbeat between the pair of consecutive heartbeat intervals as a PVC candidate or an APC candidate if the difference between the pair of consecutive heartbeat intervals is larger than a product of a first factor and the average of heartbeat intervals and the average of the pair of consecutive heartbeat intervals is within a predetermined range, wherein an upper limit of the predetermined range is a product of a second factor and the average of heartbeat intervals and a lower limit of the predetermined range is a product of a third factor and the average of heartbeat intervals, wherein the processor is further configured to calculate a first pulse interval irregularity among the heartbeat intervals excluding the pair of consecutive heartbeat intervals associated with the PVC candidate or the APC candidate, and determine there is an AF detected from the physiological signals in response to a determination that the first pulse interval irregularity is larger than a threshold.

9. The apparatus according to claim 8, wherein the processor further calculates a second pulse interval irregularity among the heartbeat intervals between the pairs of consecutive heart pulses in the sequence of heart pulses after the processor acquires physiological signals, and determines there is no AF detected from the physiological signals in response to a determination that the second pulse interval irregularity is not larger than the threshold.

10. The apparatus according to claim 8, wherein the processor further searches a previous heartbeat interval consecutive to a former heartbeat interval of the pair of consecutive heartbeat intervals, and examines the previous heartbeat interval and a later heartbeat interval of the pair of consecutive heartbeat intervals to identify whether the heartbeat between the previous heartbeat interval and the later heartbeat interval is the PVC candidate or the APC candidate.

11. The apparatus according to claim 8, wherein the first pulse interval irregularity comprises a NADiff or a RMSSD of heartbeat intervals.

12. The apparatus according to claim 8, wherein a value of the first factor is ranging from 0.3 to 0.4.

13. The apparatus according to claim 8, wherein a value of the second factor is ranging from 0.8 to 0.95.

14. The apparatus according to claim 8, wherein a value of the third factor is ranging from 1.1 to 1.2.

15. A non-transitory computer readable medium comprising a computer program to be loaded by an electronic apparatus to execute steps of:
    acquiring physiological signals of a human comprising a sequence of heart pulses;
    calculating an average of heartbeat intervals between pairs of consecutive heart pulses in the sequence of heart pulses;
    examining each pair of consecutive heartbeat intervals to determine whether a difference between the pair of consecutive heartbeat intervals is larger than a product of a first factor and the average of heartbeat intervals and determine whether an average of the pair of consecutive heartbeat intervals is within a predetermined range, wherein an upper limit of the predetermined range is a product of a second factor and the average of heartbeat intervals and a lower limit of the predetermined range is a product of a third factor and the average of heartbeat intervals; and
    identifying a heartbeat between the pair of consecutive heartbeat intervals as a PVC candidate or an APC candidate in response to a determination that the difference between the pair of consecutive heartbeat intervals is larger than the product of the first factor and the average of heartbeat intervals and the average of the pair of consecutive heartbeat intervals is within the predetermined range,
    wherein after the step of identifying the heartbeat between the pair of consecutive heartbeat intervals as the PVC candidate or the APC candidate, the steps further comprise:
    calculating a first pulse interval irregularity among the heartbeat intervals excluding the pair of consecutive heartbeat intervals associated with the PVC candidate or the APC candidate; and
    determining there is an atrial fibrillation (AF) detected from the physiological signals in response to a determination that the first pulse interval irregularity is larger than a threshold.

* * * * *